United States Patent [19]

Armstrong

[11] 4,118,813
[45] Oct. 10, 1978

[54] SLEEP TRAINING PILLOW FOR THE PREVENTION OF SNORING

[76] Inventor: Nolen L. Armstrong, 3131 NW. Expressway, Oklahoma City, Okla. 73112

[21] Appl. No.: 740,419

[22] Filed: Nov. 10, 1976

[51] Int. Cl.² ............................................. A47G 9/00
[52] U.S. Cl. .......................................... 5/337; 5/338; 5/341
[58] Field of Search .......................... 5/337, 338, 341; D6/201, 204

[56] References Cited

U.S. PATENT DOCUMENTS

| D. 168,139 | 11/1952 | Brady | D6/201 |
|---|---|---|---|
| 2,234,506 | 3/1941 | Sistig | 5/338 |
| 2,295,906 | 9/1942 | La Cour | 5/338 |
| 2,940,087 | 6/1960 | Kiefer | 5/338 |
| 3,243,828 | 4/1966 | McCarthy | 5/341 |
| 3,753,264 | 8/1973 | Grenier | 5/338 R |
| 3,757,365 | 9/1973 | Kretchmer | 5/338 |

*Primary Examiner*—Victor N. Sakran
*Attorney, Agent, or Firm*—Dunlap, Codding & McCarthy

[57] ABSTRACT

An improved sleep training pillow designed to train a person to sleep in a position to prevent snoring, the sleep training pillow comprising a head support platform that has a pillow support surface and a face support surface. The face support surface has a high end and a low end, and the face support surface is inclined downwardly from the high end to the low end at an angle of incline relative to the pillow support surface. The head support platform has a relief cavity near the low end thereof extending from the face support surface into the head support platform. Each side of the head support platform may be shaped to form a shoulder relief curvature.

6 Claims, 3 Drawing Figures

SLEEP TRAINING PILLOW FOR THE PREVENTION OF SNORING

BACKGROUND OF THE INVENTION

1. Field of the Invention

The present invention relates generally to training devices and more particularly, but not by way of limitation, to an improved device for training people to sleep in a position which will prevent snoring.

2. Brief Description of the Prior Art

Studies of anatomy shown that when deep sleep occurs, especially with the added effect of a sleeping medication or the like, the jaw muscles of a person relax and the person's tongue tends to droop dependently. Obstruction to the person's air passage may then occur at the glottis, and the well-known phenomenon of snoring results. Snoring noises are caused by the vibration of the tongue and throat structures as the person's lungs attempt to push air out and past the obstruction.

While snoring is generally lightly regarded, it may present a serious problem, both in terms of the impeded breathing capability of the person so affected, and in terms of the objections raised by others who may be awakened by the snoring noise. In any event and for whichever reason, the problem of preventing snoring has been studied without a satisfactory solution to date, as all of the known prior art methods and devices have various drawbacks. Prior art devices usually impose a penalty upon the snoring sleeper, such as the rude awakening thereof. This does not prevent snoring, but simply interrupts the sleep of the snoring person. Thus, no means has heretofore been known to prevent snoring while affording the person a healthy, unimpeded night's rest.

SUMMARY OF THE INVENTION

The present invention provides a sleep training pillow that is designed to train a person to sleep in a comfortable position which will prevent snoring in almost all instances and under all conditions. The sleep training pillow comprises a head support platform that has a pillow support surface and a face support surface disposed at an angle of incline relative to the pillow support surface. The face support surface is sloped downwardly from a high end thereof to a low end, and a relief cavity is disposed near the low end in a manner that the relief cavity intersects the face support surface.

A person may be trained to use the sleep training pillow by lying in a position that places the head on the face support surface of the head support platform. In the preferred embodiment, the angle of incline is approximately 20°, causing the head to be positioned at this incline angle. The relief cavity is disposed near the nose and mouth of the sleeper, allowing easy access to air for breathing. In this position, the jaw and tongue of the sleeper are positioned so that the tongue is prevented from obstructing the air passage to the lungs, thus preventing the noise of snoring.

Accordingly, an object of the present invention is to provide a sleep training device to train the person using it to sleep in a position that will prevent snoring.

Another object of the present invention is to provide a sleep training device that will permit the person using it to sleep in a comfortable position while preventing snoring.

Another object of the present invention is to provide a sleep training device that promotes better sleeping, better aeration of the lungs, and overall better health of the user thereof.

Other objects, advantages and features of the present invention will be apparent from the following detailed description of the preferred embodiment when read with the accompanying drawings and the appended claims.

DESCRIPTION OF THE PREFERRED EMBODIMENT

The present invention comprises a sleep training device that is designed to train a person using it to sleep in a comfortable position which will prevent snoring in almost all instances or conditions. Of course, the sleep training pillow of the present invention may be used in an ongoing fashion as a pillow, but the present invention teaches a training device that will train the person to sleep in a position even when using a regular pillow that will prevent snoring.

Figure 1:
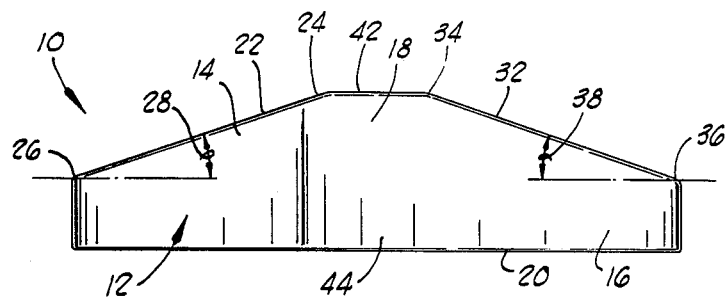
FIG. 1 is a side elevational view of the sleep training pillow of the present invention.
Figure 2:
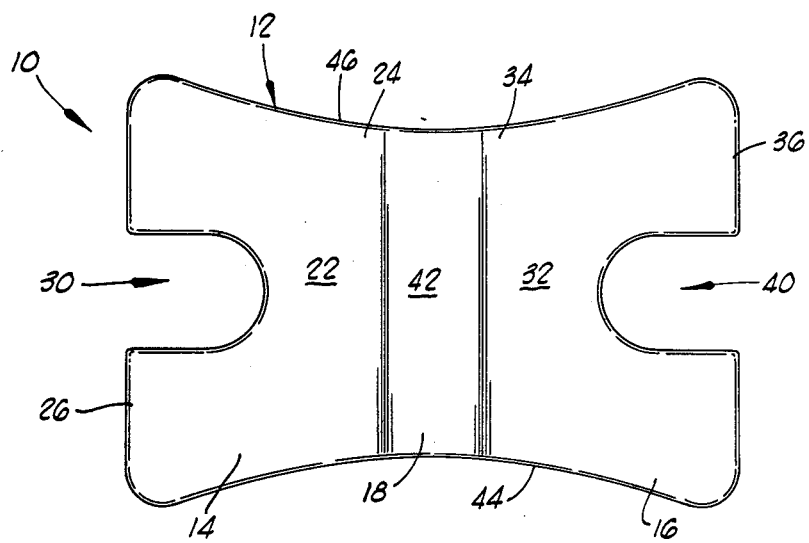
FIG. 2 is a top plan of the sleep training pillow shown in FIG. 1.

Referring now to the drawings and to FIGS. 1 and 2 in particular, shown therein and designated by the general reference numeral 10, is a sleep training pillow constructed in accordance with the present invention. The pillow 10 comprises a head support platform 12 that in the preferred form is a single piece or of unitary construction, but for purposes of description, the head support platform 12 will be described as comprising a first end member 14, a second end member 16 and a central portion member 18. The head support platform 12 has a pillow support surface, or bottom surface 20 that serves as the base for the pillow 10. The first end member 14, forming one end of the head support platform 12, has a first face support surface, or first top surface 22 that is generally a planar surface that extends downwardly from a high end 24 to a low end 26 thereof. The first face support surface 22 has an angle of incline 28 relative to the pillow support surface 20. That is, if the plane of the pillow support surface 20 and the plane of the first face support surface 22 were to be extended, the planes would converge at an angle equal to the angle of incline 28.

At the low end 26 of the first end member 14, a first relief cavity 30 is disposed in the head support platform 12 so as to intersect the first face support 22. As viewed from the top in FIG. 2, the first relief cavity 30 appears as a notch in the low end 26, or as an aperture in the first face support surface 22 formed by the first relief cavity 30 as it extends therefrom into the head support platform 12.

The second end member 16, forming the other end of the head support platform 12, has a second face support surface or second top surface 32 that is generally a planar surface and which extends downwardly from a high end 34 to a low end 36 thereof. The second face support surface 32 has an angle of incline 38 relative to the pillow support surface 20. That is, in like manner to the first face support surface 22, if the plane of the pillow support surface 20 and the plane of the second face support surface 32 were to be extended, the planes would converge at an angle equal to the angle of incline 38. As shown in FIG. 1, the second face support surface 32 has a reverse slope to that of the first face support surface 22, and as will be pointed out below, the angle of incline 28 is generally equal to the angle of incline 38.

At the low end 36 of the second end member 16, a second relief cavity 40 is disposed in the head support platform 12 in like manner to that which has been described for the first relief cavity 30. That is, the second relief cavity 40 is disposed to intersect the second face support surface 32, and as viewed from the top in FIG. 2, the second relief cavity 40 appears as a notch in the low end 36, or as an aperture in the second face support surface 32 formed by the second relief cavity 40 as it extends therefrom into the head support platform 12.

In the preferred form, the first end member 14 and the second end member 16 are connected by the central portion member 18 which is connected to the high end 24 and the high end 34 of the first and second end members 14 and 16 respectively. The central portion member 18 has an upper surface 42 that forms a central support surface.

The head support platform 12 has a first side 44 and a second side 46 which are shaped in a curved fashion so that these side surfaces form relief curvatures for a purpose that will be made clear below.

In the preferred form, the head support platform 12 is integrally formed and is of unitary construction, being made from a flexible, deformable material, such as polyurethane foam plastic. It will be apparent that there are many materials that will suffice. Different people vary considerably in their desire for pillow softness or firmness, and the present invention is not intended to be limited by the choice of material used. Generally speaking, the head support platform 12 should be sufficiently firm, yet readily deformable by the effective resting weight of the head of a user of the pillow. The term "effective resting weight" means that force which is exerted by the head of a user of the pillow, it being clear that a pillow should also be supportive of the head. Obviously, the amount of deformation is determined by the material of construction to meet the softness, or firmness desired by a particular user.

Figure 3:
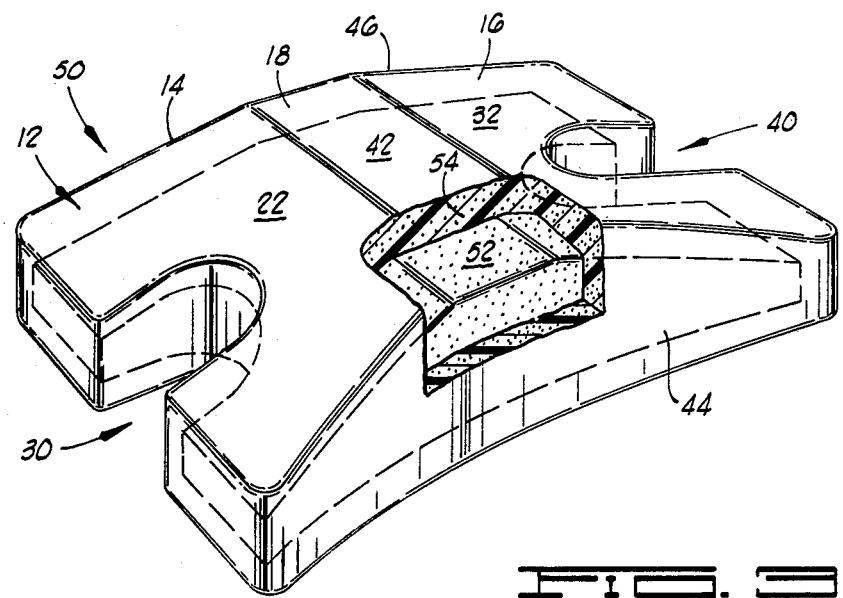
FIG. 3 is a perspective view in partial cut away detail of another embodiment of the sleep training pillow of the present invention.

The manner of use of the sleep training pillow 10 will be described below, but at this point an alternate construction of the present invention will be described with reference to FIG. 3 wherein is shown another sleep training pillow 50 constructed in accordance with the present invention. The shape of the sleep training pillow 50 is generally identical to that described above for the sleep training pillow 10, and like numerals are used in FIG. 3 to identify the corresponding portions of the sleep training pillow 50, with only the difference of construction to be described herein.

The sleep training pillow 50 has a shaped retaining core 52 that is made of a semi-rigid material. An outer layer 54 is formed about the shape retaining core 52 as shown. The overall shape of the core 52 generally conforms to that which was described above for the sleep training pillow 10, and the addition of the layer 54, being of a generally uniform thickness, conforms the shape of the pillow 50 to that of the pillow 10. The term "semi-rigid" is not meant to be limiting, but merely descriptive of the degree of flexibility of the core 52 relative to the layer 54. As was described above for the material of construction for the sleep training pillow 10, the material selected for the layer 54 should be readily deformable by, and supportive of, the effective resting weight of the head of a user of the pillow.

Turning now to a discussion of the use of the pillow 10 as a training device to train a person to sleep in a comfortable position which will prevent snoring, a person is instructed to lie on his side or abdomen with the head on either end of the pillow 10. It will be understood that the pillow 50 will be used in identical fashion to that of the pillow 10, and a description of the use of the pillow 10 will therefore be sufficient for both of the described pillows. The incline angles 28 and 38 are preferably established at approximately 20°, although the exact amount of angle may vary with the preference of the user. It has been found that an angle between about 15° and about 25° is usually sufficient for the purposes of this invention.

During use of the pillow 10, the user's head rests on one of the face support surfaces, 22 or 32, with the face of the user disposed toward the low end, 26 or 36 respectively, of the face support surface, 22 or 32. The shoulder of the user engages one of the sides, 44 or 46, of the pillow 10 such that the body of the user extends away from the side, 44 or 42, engaged by the user's shoulder.

As the head of the user is placed on the first face support surface 22 or on the second face support surface 32, the face of the user will be angled downwardly at approximately the angle corresponding to the value of the angle of incline. Since the user will only be using one end of the pillow 10 at a given time, the description of the use of the pillow 10 will be confined to the case where the user has placed his head on the first end member 14 and the first face support surface 22. In this position, the first relief cavity 30 is positioned to enable the nose and mouth of the user to be free, allowing easy access to air for breathing. This also prevents upward pressure of the bed clothes at the nose and mouth area from interfering with comfortable breathing.

As the user of the pillow lies with his head on the inclined portion, the first face support surface 22, the jaw and tongue members will relax during sleep. Consequently, these members are permitted to more readily fall forward and downwardly, insuring unobstructed passage of air to the lungs and preventing the noise of snoring. Of course, if the user turns in his sleep, he will normally turn to the other end of the pillow 10, and the same results will be achieved. As the individual continues to use the sleep training pillow 10 for a period of time (usually for a few months), it is expected that better sleeping and better aeration of the lungs will occur; consequently, the user will be afforded better health. Further, it has been found that individuals that have used the sleep training pillow 10 for a period of time are trained to sleep in the position of having an inclined head, even when using a regular pillow. Since it is the inclination of the head during sleep that prevents snoring, the individual has been trained to sleep in a comfortable position which will prevent snoring even when not using the training pillow 10.

The reason for the curved shape of the first and second sides 44 and 46 of the sleep training pillow 10 is to permit a more comfortable positioning of the pillow beneath the head of the user without unduly interfering with the shoulder of the user. That is, the shape of the first and second sides 44, 46 are formed in the shape of a shoulder relief curvature, the exact curvature of which is not controlling.

While the size of the pillow is not limiting to the present invention, it has been found that a good size for the pillow is from about 24 to 30 inches in length, and from about 15 to 18 inches in width. The reason for the suggested size is that this will afford a sleep training pillow that will fit in a standard size pillow case, and the first and second relief cavities 30, 40 will allow room for the pillow case to drop into these recesses at each end.

It is evident that the presently described invention provides a sleep training device that is useful to train a person using it to sleep in a position that will prevent his snoring. Also, it is evident that the other objects, advantages and features described hereinabove are fully met by the described invention. It will be recognized that changes may be made in the construction and the arrangement of the parts or elements of the embodiments disclosed herein without departing from the spirit and the scope of the invention as defined in the following claims.

What is claimed is:

1. A sleep training pillow for positioning a person's head along a predetermined incline with the face angled downwardly, the pillow characterized as having a pillow support surface and comprising:
    a first end member having a planar first face support surface, the first face support surface disposed to have a first angle of incline relative to the pillow support surface between 15° and 25°, and the first face support surface characterized as extending a sufficient distance to support the person's head positioned thereon such that the face of the person will be angled downwardly at approximately an angle corresponding to the value of the first angle of incline, and a second end member having a planar second face support surface, the second face support surface disposed to have a second angle of incline relative to the pillow support surface between 15° and 25°, and the second face support surface characterized as extending a sufficient distance to support the person's head positioned thereon such that the face of the person will be angled downwardly at approximately an angle corresponding to the value of the second angle of incline, the second angle of incline being reverse sloped relative to the first face support surface.

2. The pillow of claim 1 wherein:
    the first end member has a high end and a low end, the first face support surface being sloped from the high end downwardly to the low end, and the first end member having a first relief cavity disposed in the low end and intersecting the first face support surface; and
    the second end member has a high end and a low end, the second face support surface being sloped from the high end downwardly to the low end, and the second end member having a second relief cavity disposed in the low end and intersecting the second face support surface.

3. The pillow of claim 2 further characterized as comprising:
    a central portion having a planar support surface and connected to the high end of the second end member, the central support surface being generally parallel to the pillow support surface.

4. The pillow of claim 3 further characterized as having a first side and a second side, each of the first and second sides shaped to form a shoulder relief curvature along the sides of the pillow for a user of the pillow.

5. The pillow of claim 3 wherein the pillow is of unitary construction and formed of a flexible material that is readily deformable by, and supportive of, the effective resting weight of the head of a user of the pillow.

6. The pillow of claim 3 wherein the pillow comprises:
    a shape retaining core made of semi-rigid material;
    an outer layer formed about the shape retaining core, the outer layer made of a material that is readily deformable by, and supportive of, the effective resting weight of the head of a user of the pillow.

* * * * *